(12) United States Patent
Sun et al.

(10) Patent No.: US 12,188,862 B2
(45) Date of Patent: Jan. 7, 2025

(54) HARMONICS MICROSCOPE FOR MEASURING GLYCATED HEMOGLOBIN FRACTION OF SINGLE RED BLOOD CELL

(71) Applicant: National Taiwan University, Taipei (TW)

(72) Inventors: Chi-Kuang Sun, Taipei (TW); Xu-hao Ye, Taipei (TW)

(73) Assignee: National Taiwan University, Taipei (TW)

( * ) Notice: Subject to any disclaimer, the term of this patent is extended or adjusted under 35 U.S.C. 154(b) by 170 days.

(21) Appl. No.: 18/113,704

(22) Filed: Feb. 24, 2023

(65) Prior Publication Data

US 2024/0264073 A1    Aug. 8, 2024

(30) Foreign Application Priority Data

Feb. 6, 2023    (TW) ................. 112104082

(51) Int. Cl.
*G01N 21/31* (2006.01)
*G01N 33/49* (2006.01)
(Continued)

(52) U.S. Cl.
CPC ......... *G01N 21/3103* (2013.01); *G01N 33/49* (2013.01); *G02B 21/0032* (2013.01);
(Continued)

(58) Field of Classification Search
CPC ....... G06T 5/20; G06T 5/008; G01B 9/02091; G01J 3/027; G01J 3/2823; G01N 21/3103;
(Continued)

(56) References Cited

U.S. PATENT DOCUMENTS 4,948,248 A * 8/1990 Lehman ............. A61B 5/14551
600/323
6,922,279 B2 * 7/2005 Sun ...................... G01N 21/636
356/904
(Continued)

FOREIGN PATENT DOCUMENTS

WO    WO 2020/254550 A1 * 12/2020

*Primary Examiner* — Hoa Q Pham
(74) *Attorney, Agent, or Firm* — Demian K. Jackson; Jackson IPG PLLC

(57) ABSTRACT

A microscope is provided to measure HbA1c fraction. The microscope measures the HbA1c fraction of a single red blood cell (RBC) in a trace blood sample. The HbA1c fraction can be measured through a non-invasive way while the RBC flows in a human epidermal microvessel, too. The microscope comprises a laser device, an upright microscope, a light splitter, a light detector, and a mainframe. Unlike traditional methods, the HbA1c fraction can be measured in vitro or in vivo at the level of a single RBC. Accurate measurement is achieved. Misdiagnosis rate is reduced. The microscope provides HbA1c fractions from hundreds of RBCs, instead of averaging HbA1c fractions obtained from a large number of blood samples. Hence, the present invention is a method of detecting a HbA1c fraction of a single RBC, and is a microscope supporting blood-drawing measurement and non-invasive measurement simultaneously.

7 Claims, 4 Drawing Sheets

(51) Int. Cl.
*G02B 21/00* (2006.01)
*G02B 27/10* (2006.01)
*G02B 27/14* (2006.01)

(52) U.S. Cl.
CPC ..... *G02B 21/0064* (2013.01); *G02B 27/1013* (2013.01); *G02B 27/141* (2013.01); *G02B 27/145* (2013.01)

(58) Field of Classification Search
CPC .... G01N 21/65; G01N 33/49; G02B 21/0032; G02B 21/0064; G02B 21/0052; G02B 21/0076; G02B 21/06; G02B 21/008; G02B 27/141; G02B 27/145; A61B 5/0064; A61B 5/0071; A61B 5/0075; A61B 5/6832; A61B 5/6831; A61B 5/4836; A61B 18/18; A61N 5/06; A61N 5/0616
USPC ............. 356/39–41, 301–328, 417; 433/215; 600/473; 606/9, 13
See application file for complete search history.

(56) References Cited

U.S. PATENT DOCUMENTS

2013/0001408 A1\* 1/2013 Sun ........................ G02B 21/00
  250/578.1
2014/0012104 A1\* 1/2014 Chen ................... A61B 5/1455
  600/322
2019/0355106 A1\* 11/2019 Toussaint .............. G06T 7/0012

\* cited by examiner

HARMONICS MICROSCOPE FOR MEASURING GLYCATED HEMOGLOBIN FRACTION OF SINGLE RED BLOOD CELL

TECHNICAL FIELD OF THE INVENTION

The present invention relates to harmonics microscopy of a single red blood cell (RBC); more particularly, to realizing the detection of a glycated hemoglobin fraction (HbA1c fraction) of a single RBC and supporting blood-drawing measurement and non-invasive measurement at the same time.

DESCRIPTION OF THE RELATED ARTS

Although all current methods of blood-glucose estimation based on glycated hemoglobin can evaluate the average blood glucose level for about 3 months, it is impossible to provide any information on blood glucose fluctuation. Continuous development clearly shows that changes in blood glucose levels relate to diabetes complications, independent of the glycated hemoglobin index.

However, traditional methods are still subject to some clinical limits. For example:
1. Most existing techniques for measuring glycated hemoglobin fraction require large blood samples for measurement.
2. Some techniques based on immunolabeling can measure glycated hemoglobin fraction with a small amount of blood samples. However, the storage environment and usage requirements of test strip or kit box may limit the applications of these technologies.
3. Most existing technologies do not allow non-intrusive measurement.
4. Most current technologies are unable to achieve resolution at the level of a single red blood cell. It is therefore impossible to distinguish the contribution of glucose from other factors.

Hence, the prior arts do not fulfill all users' requests on actual use.

SUMMARY OF THE INVENTION

The main purpose of the present invention is to detect an HbA1c fraction of a single RBC as supporting blood-drawing measurement and non-invasive measurement simultaneously.

Another purpose of the present invention is to break through the measurement resolution of glycated hemoglobin fraction, where the HbA1c fraction can be measured in vitro or in vivo at the level of a single RBC with accurate measurement achieved.

Another purpose of the present invention is to provide the HbA1c fraction from hundreds of single RBCs, instead of averaging HbA1c fractions obtained from a large number of blood samples, where misdiagnosis rate is reduced.

To achieve the above purposes, the present invention is a harmonics microscope for measuring a glycated hemoglobin fraction of a single RBC, where the harmonics microscope measures an HbA1c fraction of a single RBC in a trace blood sample or measures an HbA1c fraction of a single RBC through a non-invasive way while the single RBC flows in a human epidermal microvessel; the harmonics microscope comprises a laser device, an upright microscope, a light splitter, an optical detector, and a mainframe; the laser device emits laser beams of different wavelengths; each of the laser beams has a central wavelength and a frequency to specifically optimize optical characteristics of glycated hemoglobin for measure the HbA1c fraction; the upright microscope receives the laser beams of different wavelengths from the laser device; the upright microscope projects the laser beams of different wavelengths onto the single RBC to obtain harmonic observing beams of different wavelengths; the light splitter receives the harmonic observing beams of different wavelengths from the upright microscope; the light splitter divides the harmonic observing beams into a first third harmonic generation (THG) segment, a second THG segment, a third THG segment, and a second harmonic generation (SHG) segment; the optical detector receives the first THG segment, the second THG segment, the third THG segment, and the SHG segment from the light splitter; the optical detector detects the first THG segment, the second THG segment, the third THG segment, and the SHG segment to be converted into a first THG image signal, a second THG image signal, a third THG image signal, and an SHG image signal; the mainframe receives the first THG image signal, the second THG image signal, the third THG image signal, and the SHG image signal from the optical detector; the mainframe integrates the first THG image signal, the second THG image signal, the third THG image signal, and the SHG image signal into a multispectral image; the mainframe is installed with an image processing software; and, after the image processing software receives the multispectral image through the mainframe, the HbA1c fraction of the single RBC is measured with the multispectral image. Accordingly, a novel harmonics microscope for measuring a glycated hemoglobin fraction of a single RBC is obtained.

BRIEF DESCRIPTION OF THE DRAWINGS

The present invention will be better understood from the following detailed description of the preferred embodiment according to the present invention, taken in conjunction with the accompanying drawings, in which.

DESCRIPTION OF THE PREFERRED EMBODIMENT

The following description of the preferred embodiment is provided to understand the features and the structures of the present invention.

Figure 1:
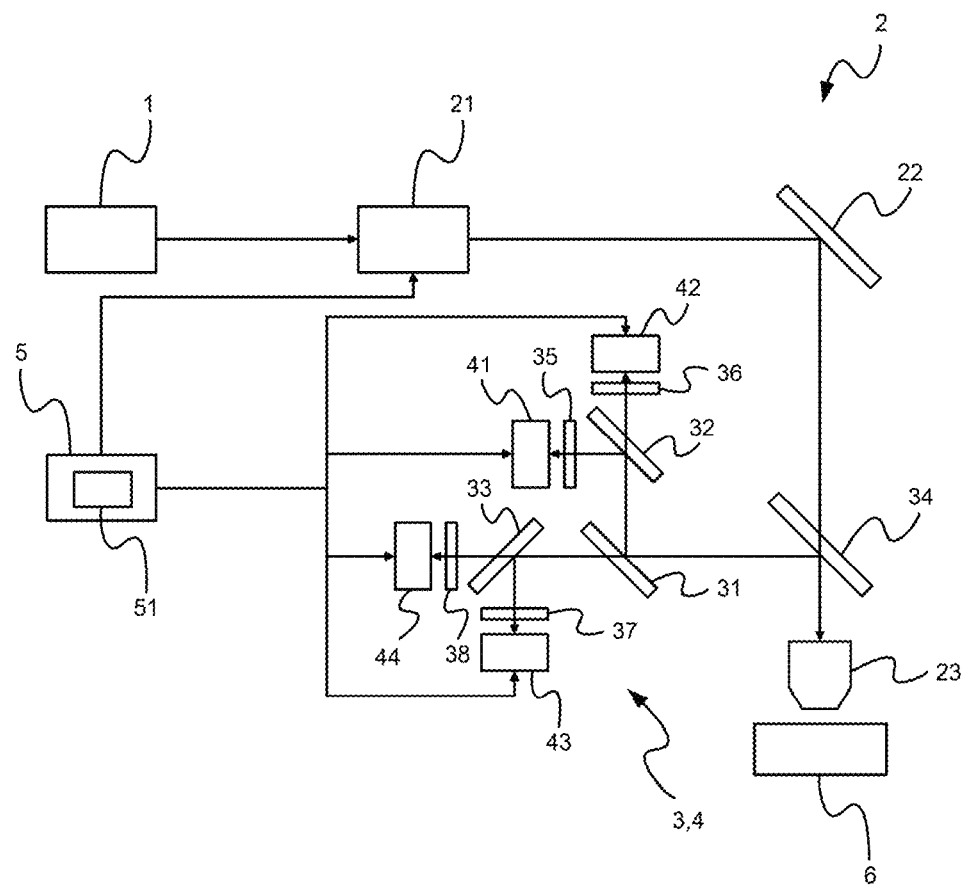
FIG. 1 is the structural view showing the preferred embodiment according to the present invention.
Figure 2A:
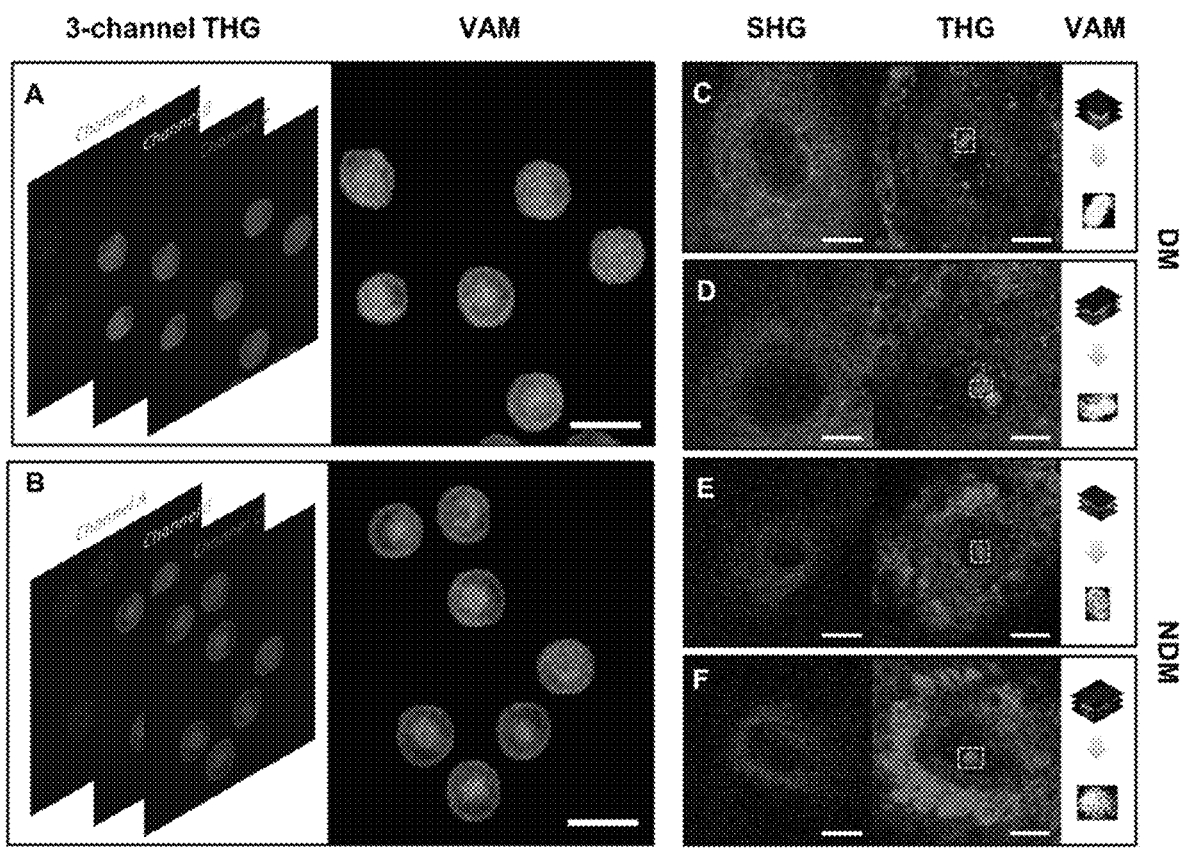
FIG. 2A and FIG. 2B are the views showing the third harmonic generation (THG) microscopy of the single red ball cell (RBC) by using the multispectral method.
Figure 2B:
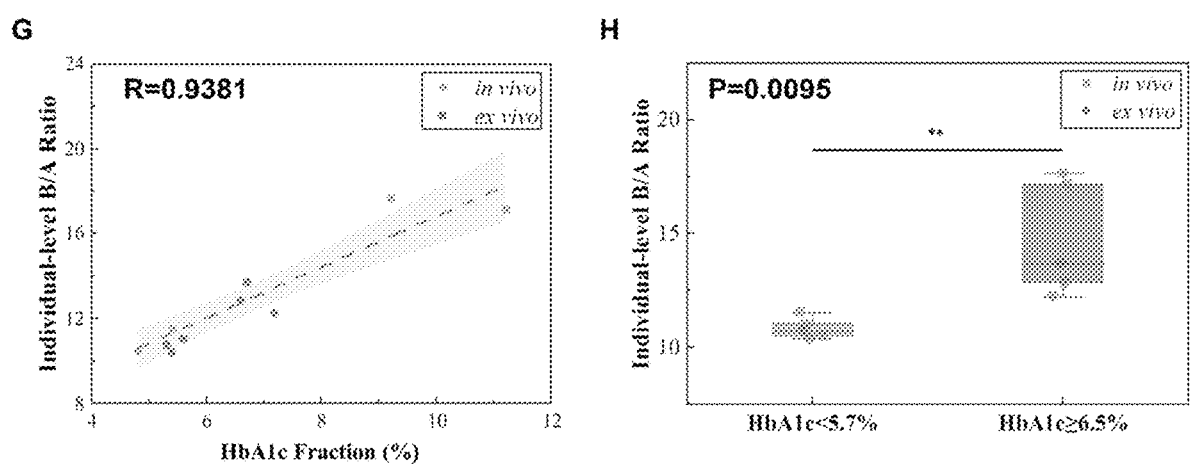
Figure 3:
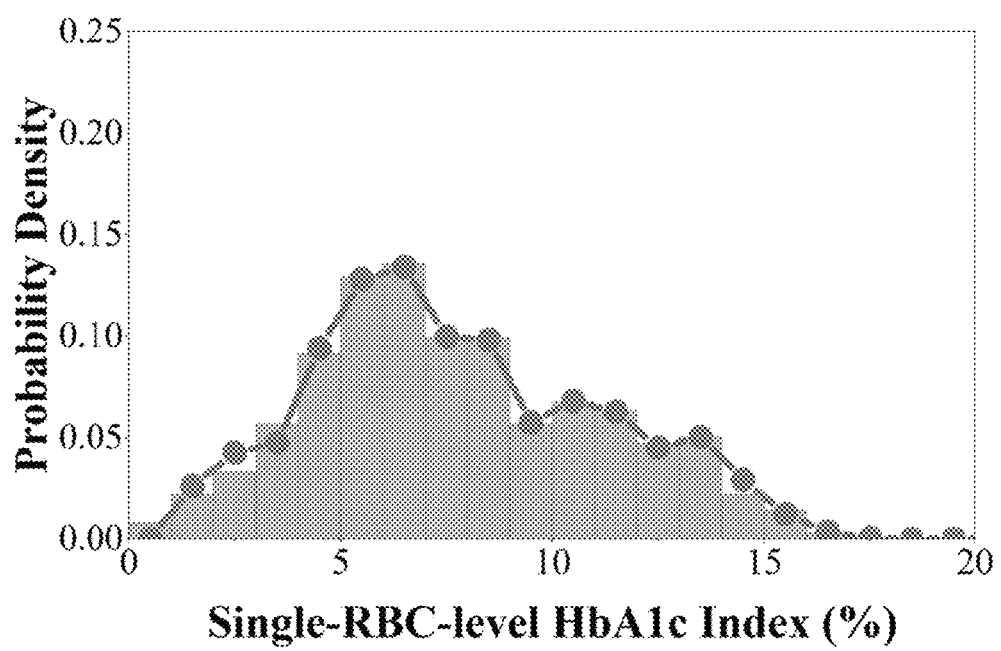
FIG. 3 is the view showing the averaging of the glycated hemoglobin fractions (HbA1c fractions) of hundreds of RBCs.

Please refer to FIG. 1 to FIG. 3, which are a structural view showing a preferred embodiment according to the present invention; a view showing a THG microscopy of a single RBC by using a multispectral method; and a view showing averaging of HbA1c fractions of hundreds of single RBCs. As shown in the figures, the present invention is a harmonics microscope for measuring an HbA1c fraction of a single RBC, where the harmonics microscope measures an HbA1c fraction of a single RBC in a trace blood sample or measures an HbA1c fraction of a single RBC through a non-invasive way while the RBC flows in a human epidermal microvessel. The harmonics microscope comprises a laser device 1, an upright microscope 2, a light splitter 3, an optical detector 4, and a mainframe 5.

The laser device 1 projects laser beams of different wavelengths, where each of the laser beams has a central wavelength and a frequency to specifically optimize optical characteristics of glycated hemoglobin for measuring the HbA1c fraction.

The upright microscope 2 receives the laser beams of different wavelengths from the laser device 1 to project the laser beams of different wavelengths onto the single RBC for generating harmonic observing beams of different wavelengths.

The light splitter 3 receives the harmonic observing beams of different wavelengths from the upright microscope 2 and divides the harmonic observing beams into a first THG segment, a second THG segment, a third THG segment, and a second harmonic generation (SHG) segment.

The optical detector 4 receives the first THG segment, the second THG segment, the third THG segment, and the SHG segment from the light splitter 3; and detects the first THG segment, the second THG segment, the third THG segment, and the SHG segment to be converted into a first THG image signal, a second THG image signal, a third THG image signal, and an SHG image signal, respectively.

The mainframe 5 receives the first THG image signal, the second THG image signal, the third THG image signal, and the SHG image signal from the optical detector 4; and integrates the first THG image signal, the second THG image signal, the third THG image signal, and the SHG image signal into a multispectral image. The mainframe 5 is installed with an image processing software; and, after the image processing software receives the multispectral image through the mainframe, the HbA1c fraction of the single RBC is measured with the multispectral image. Thus, a novel harmonics microscope that measures the HbA1c fraction of a single RBC is obtained.

The following descriptions of the state-of-uses are provided to understand the features and the structures of the present invention.

In a state-of-use, the laser device 1 has a central wavelength of 1,266 nanometers (nm), a frequency with a full width at half maximum (FWHM) of 90 nm, and a pulse width of 37 femtoseconds.

In a state-of-use, the upright microscope 2 comprises a scanner 21, a mirror 22, and an objective lens 23. The scanner 21 receives laser beams of different wavelengths from the laser device 1 and scans the laser beams of different wavelengths; the mirror 22 receives the scanned laser beams of different wavelengths from the scanner 21 and reflects there; and the objective lens 23 receives the scanned laser beams of different wavelengths from the mirror 22 to focus and project the scanned laser beams of different wavelengths onto the observes sample 6, i.e. the single RBC.

The present invention sets a filter plate in front of the optical detector 4 for optimization; and, with the detection of the stimulated nonlinear signals in a reverse manner, the spectral responses of different molecules are visualized differentially by dividing the backward-collected THG spectra to achieve the identification of specific molecules. In a state-of-use, the light splitter 3 comprises a first dichroic beamsplitter 31, a second dichroic beamsplitter 32, a third dichroic beamsplitter 33, the fourth dichroic beamsplitter 34, a first bandpass filter 35, a second bandpass filter 36, a third bandpass filter 37, and a fourth bandpass filter 38. The first dichroic beamsplitter 31 receives the first THG segment, the second THG segment, the third THG segment, and the SHG segment from the fourth dichroic beamsplitter 34, and separates the first THG segment and the second THG segment from the third THG segment and the SHG segment; the second dichroic beamsplitter 32 receives the first THG segment and the second THG segment from the first dichroic beamsplitter 31, and separates the first THG segment from the second THG segment; the third dichroic beamsplitter 33 receives the third THG segment and the SHG segment from the second dichroic beamsplitter 32, and separates the third THG segment from the SHG segment; the fourth dichroic beamsplitter 34 receives the harmonic observing beams of different wavelengths from the upright microscope wavelength 2, and divides the harmonic observing beams of different wavelengths into the first THG segment, the second THG segment, the third THG segment, and the SHG segment; the first bandpass filter 35 receives the first THG segment from the second dichroic beamsplitter 32, and filters out stray light from the first THG segment; the second bandpass filter 36 receives the second THG segment from the second dichroic beamsplitter 32, and filters out stray light from the second THG segment; the third bandpass filter 37 receives the third THG segment from the third dichroic beamsplitter 33, and filters out stray light from the third THG segment; and the fourth bandpass filter 38 receives the SHG segment from the third dichroic beamsplitter 33, and filters out stray light from the second THG segment.

In a state-of-use, the first THG segment has a wavelength of 400 nm~410 nm and a central wavelength of 405 nm; the second THG segment has a wavelength of 410 nm~418 nm and a central wavelength of 414 nm; the third THG segment has a wavelength of 418 nm~500 nm; and the SHG segment has a wavelength of 500 nm~700 nm.

In a state-of-use, a first THG segment characterizes signals provided by hemoglobin; a second THG segment characterizes signals provided by glycated hemoglobin; and an HbA1c fraction is presented by a ratio of an electrical signal strength of a second THG segment to that of the first THG segment.

In a state-of-use, the optical detector 4 comprises a first photodetector 41, a second photodetector 42, a third photodetector 43, and a fourth photodetector 44. The first photodetector 41 detects the first THG segment to be correspondingly converted into an electrical signal of the first THG image signal; the second photodetector 42 detects the second THG segment to be correspondingly converted into an electrical signal of the second THG image signal; the third photodetector 43 detects the third THG segment to be correspondingly converted into an electrical signal of the third THG image signal; and the fourth photodetector 44 detects the SHG segment to be correspondingly converted into an electrical signal of the SHG image signal.

In a state-of-use, the first to the fourth photodetectors 41~44 are photomultiplier tubes.

On using the present invention, a THG microscopy of a single RBC is shown by using a multispectral method with a different level of glycated hemoglobin of the RBC shown in a different color, as shown in FIG. 2A. In FIG. 2B, the statistical result shows the HbA1c fractions of the single RBCs obtained through the present invention.

In FIG. 3, HbA1c fractions of hundreds of single RBCs are averaged to obtain the distribution of averaged HbA1c fractions as well as the HbA1c fractions of single RBCs, which is of great help to improve the screening and diagnosis of diabetes.

Unlike traditional methods, the present invention breaks through the measurement resolution of glycated hemoglobin fraction. The glycated hemoglobin fraction can be measured in vitro or in vivo at the level of a single RBC. Accurate measurement is achieved. Misdiagnosis rate is reduced. Nevertheless, the present invention provides glycated hemoglobin fractions from hundreds of RBCs, instead of averaging the glycated hemoglobin fractions obtained from a large number of blood samples. Hence, the present invention is a method of detecting a glycated hemoglobin fraction of a single RBC, and is a harmonics microscope supporting blood-drawing measurement and non-invasive measurement at the same time.

To sum up, the present invention is a harmonics microscope for measuring a glycated hemoglobin fraction of a single RBC, where the measurement resolution of glycated hemoglobin fraction is broken through and a glycated hemoglobin fraction is measured in vitro or in vivo at the level of a single RBC with accurate measurement achieved; and glycated hemoglobin fractions are provided from hundreds of single RBCs, instead of averaging glycated hemoglobin fractions obtained from a large number of blood samples, while misdiagnosis rate is reduced.

The preferred embodiment herein disclosed is not intended to unnecessarily limit the scope of the invention. Therefore, simple modifications or variations belonging to the equivalent of the scope of the claims and the instructions disclosed herein for a patent are all within the scope of the present invention.

What is claimed is:

1. A harmonics microscope for measuring a glycated hemoglobin fraction (HbA1c fraction) of a single red blood cell (RBC),
    said harmonics microscope measuring said HbA1c fraction of a single RBC in a trace blood sample,
    said harmonics microscope measuring an HbA1c fraction of said single RBC through a non-invasive way while said single RBC flows in a human epidermal microvessel,
    said harmonics microscope comprising
        a laser device,
            said laser device emitting laser beams of different wavelengths,
            each of said laser beams having a central wavelength and a frequency to specifically optimize optical characteristics of glycated hemoglobin to measure said HbA1c fraction;
        an upright microscope,
            said upright microscope receiving said laser beams of different wavelengths from said laser device,
            said upright microscope projecting said laser beams of different wavelengths onto a single RBC to obtain harmonic observing beams of different wavelengths;
        a light splitter,
            said light splitter receiving said harmonic observing beams of different wavelengths from said upright microscope,
            said light splitter dividing said harmonic observing beams into a first third harmonic generation (THG) segment, a second THG segment, a third THG segment, and a second harmonic generation (SHG) segment;
        an optical detector,
            said optical detector receiving said first THG segment, said second THG segment, said third THG segment, and said SHG segment from said light splitter,
            said optical detector detecting said first THG segment, said second THG segment, said third THG segment, and said SHG segment to be converted into a first THG image signal, a second THG image signal, a third THG image signal, and an SHG image signal; and
        a mainframe,
            said mainframe receiving said first THG image signal, said second THG image signal, said third THG image signal, and said SHG image signal from said optical detector,
            said mainframe integrating said first THG image signal, said second THG image signal, said third THG image signal, and said SHG image signal into a multispectral image,
        wherein said mainframe has an image processing software; and, after said image processing software receives said multispectral image through said mainframe, said HbA1c fraction of said single RBC is measured with said multispectral image,
        wherein said first THG segment characterizes signals provided by hemoglobin;
        said second THG segment characterizes signals provided by glycated hemoglobin; and
        said HbA1c fraction is a ratio of an electrical signal strength of said second THG segment to that of said first THG segment.

2. The harmonics microscope according to claim 1, wherein said laser device has said central wavelength of 1,266 nanometers (nm), said frequency with a full width at half maximum (FWHM) of 90 nm, and a pulse width of 37 femtoseconds.

3. The harmonics microscope according to claim 1, wherein said upright microscope comprises
    a scanner,
        said scanner receiving said laser beams of different wavelengths from said laser device and scanning said laser beams of different wavelengths;
    a mirror,
        said mirror receiving said scanned laser beams of different wavelengths from said scanner and reflecting there; and
    an objective lens,
        said objective lens receiving said laser beams of different wavelengths from said mirror to focus and project said scanned laser beams of different wavelengths onto said single RBC.

4. The harmonics microscope according to claim 1, wherein said light splitter comprises
    a first dichroic beamsplitter,
        said first dichroic beamsplitter receiving said first THG segment, said second THG segment, said third THG segment, and said SHG segment from a fourth dichroic beamsplitter and separating said first THG segment and said second THG segment from said third THG segment and said SHG segment;
    a second dichroic beamsplitter,
        said second dichroic beamsplitter receiving said first THG segment and said second THG segment from said first dichroic beamsplitter and separating said first THG segment from said second THG segment;
    a third dichroic beamsplitter,
        said third dichroic beamsplitter receiving said third THG segment and said SHG segment from said second dichroic beamsplitter and separating said third THG segment from said SHG segment;
    said fourth dichroic beamsplitter, said fourth dichroic beamsplitter receiving said harmonic observing beams of different wavelengths from said upright microscope and dividing said harmonic observing beams of different wavelengths into said first THG segment, said second THG segment, said third THG segment, and said SHG segment;

a first bandpass filter,
said first bandpass filter receiving said first THG segment from said second dichroic beamsplitter and filtering out stray light from said first THG segment;

a second bandpass filter,
said second bandpass filter receiving said second THG segment from said second dichroic beamsplitter and filtering out stray light from said second THG segment;

a third bandpass filter,
said third bandpass filter receiving said third THG segment from said third dichroic beamsplitter and filtering out stray light from said third THG segment; and a fourth bandpass filter,
said fourth bandpass filter receiving said SHG segment from said third dichroic beamsplitter and filtering out stray light from said SHG segment.

5. The harmonics microscope according to claim 4, wherein said first THG segment has a wavelength of 400 nm~410 nm and a central wavelength of 405 nm; said second THG segment has a wavelength of 410 nm~418 nm and a central wavelength of 414 nm; said third THG segment has a wavelength of 418 nm~500 nm; and said SHG segment has a wavelength of 500 nm~700 nm.

6. The harmonics microscope according to claim 1, wherein said optical detector comprises
a first photodetector,
said first photodetector detecting said first THG segment to be correspondingly converted into an electrical signal of said first THG image signal;

a second photodetector,
said second photodetector detecting said second THG segment to be correspondingly converted into an electrical signal of said second THG image signal;

a third photodetector,
said third photodetector detecting said third THG segment to be correspondingly converted into an electrical signal of said third THG image signal; and a fourth photodetector,
said fourth photodetector detecting said SHG segment to be correspondingly converted into an electrical signal of said SHG image signal.

7. The harmonics microscope according to claim 6, wherein said first to said fourth photodetectors are photomultiplier tubes.

* * * * *